United States Patent
Li

(10) Patent No.: US 9,067,016 B2
(45) Date of Patent: Jun. 30, 2015

(54) INFUSION MONITORING DEVICE AND METHOD FOR MONITORING THE INFUSION DRIPPING RATE AND ALARMING FOR THE IRREGULARITIES OF THE INFUSION

(75) Inventor: Yimin Li, Shenzhen (CN)

(73) Assignee: Peng Chen, Dublin, OH (US)

( * ) Notice: Subject to any disclaimer, the term of this patent is extended or adjusted under 35 U.S.C. 154(b) by 352 days.

(21) Appl. No.: 13/531,492

(22) Filed: Jun. 22, 2012

(65) Prior Publication Data
US 2013/0184675 A1      Jul. 18, 2013

(51) Int. Cl.
*A61M 5/168*      (2006.01)
*A61M 5/14*      (2006.01)

(52) U.S. Cl.
CPC ......... *A61M 5/16854* (2013.01); *A61M 5/1411* (2013.01); *A61M 5/16831* (2013.01); *A61M 2205/18* (2013.01); *A61M 2205/3317* (2013.01); *A61M 2205/3334* (2013.01)

(58) Field of Classification Search
CPC ............ A61M 5/168; A61M 5/16831; A61M 5/16877; A61M 5/16886; A61M 5/1689
USPC ..................................................... 604/65, 67
See application file for complete search history.

(56) References Cited

U.S. PATENT DOCUMENTS

| | | | |
|---|---|---|---|
| 3,375,716 A | 4/1968 | Hersch | 73/304 |
| 5,135,485 A | 8/1992 | Cohen et al. | 604/67 |
| 5,166,667 A | 11/1992 | Jen | 340/606 |
| 6,562,012 B1 * | 5/2003 | Brown et al. | 604/253 |
| 6,736,801 B1 * | 5/2004 | Gallagher | 604/253 |
| 7,492,167 B2 * | 2/2009 | Reich et al. | 324/663 |

* cited by examiner

*Primary Examiner* — Laura Bouchelle

(57) ABSTRACT

The present invention discloses an intravenous infusion monitoring device for monitoring the infusion dripping rate. This device is attached to an infusion tube above the dripping chamber, including two polar plates forming a capacitor, a capacitance measurement unit electrically connected to the capacitor, a micro control unit (MCU) configured to collect data from the capacitance measure unit and analysis and display the infusion dripping rate. A method for monitoring infusion rate includes setting the infusion solution surface to a specific height in the dripping chamber so that the infusion solution in the tube is conducted and have a pulse change of the capacitance at the moment when a droplet drips down, determining the cycle of the pulse corresponding to the infusion rate and displaying the dripping rate by LCD screen, and alarming when the infusion irregularities occurs such as too fast, too slow or fully stop.

7 Claims, 4 Drawing Sheets

INFUSION MONITORING DEVICE AND METHOD FOR MONITORING THE INFUSION DRIPPING RATE AND ALARMING FOR THE IRREGULARITIES OF THE INFUSION

BACKGROUND

1. Technical Field

The present invention relates to the field of electronic medical technology. More particularly, the present invention relates to a portable and non-power supplied electronic device and method for monitoring the intravenous infusion dripping flow rate in real time and generating alarm signals for the irregularities of the intravenous infusion.

2. Related Art

Intravenous gravity infusions are widely used medical treatment, and especially seriously ill patient often require long hours of continuous monitoring by caregivers. When the infusion solution is depleted or some irregularities happen during the infusion processing, the caregiver need promptly notify a medical staff person to change the infusion solution or remove the needle from the intravenous vessel. Time is very essential for preventing the complications such as blood backflow or air bubbles trapped in the infusion tube, but the continual monitoring of the infusion solution level by people is extremely inconvenient and burdensome for the caregiver. It might be very danger if the caregiver neglects their duty, especially during the night when the caregiver may be drowsy. The infusion dripping rate is one of the most important parameters for intravenous therapy. There are stringent requirements for infusion rate among certain patients such as the elderly, pediatric patients or patients with cardiopulmonary diseases, as well as when special medical solution is used. Large variations of the infusion rate due to poor performance of the infusion device, human factors or equipment failures could happen during the infusion process, for example, patients arbitrarily tune fast the solution dripping rate during the infusion process, or the infusion control valve becomes loose, the infusion needle moves out of the intravenous vessel, the blood is clogged inside of the needle bucket, the infusion needle rotates in the venous, or the blood pressure changes during the infusion process. All these kind of scenario might lead to deleterious consequences, or even cause unconsciousness and death of the patients under severe conditions. To help combat this problem, a variety of alarm devices have been developed to monitor and control the infusion dripping rate in clinic.

The existing infusion monitoring technologies for infusion dripping rate (or flow rate) might mainly include ultrasound, Of optical perception technologies, or detecting the fluid levels of the intravenous infusion container as shown in Cohen (U.S. Pat. No. 5,135,485).

All the current intravenous infusion monitoring device have failed to create a feasible solution to make a small, portable, highly energy saved and ultra-sensitive intravenous infusion monitoring device be cable of detecting and displaying the intravenous infusion dripping flow rate in real time.

Devices based on ultrasound technology usually involve placing a pair of ultrasonic transceivers at both sides of the infusion dripping chamber. Based on the principle that solution droplets cause attenuation or refraction of ultrasound wave, a group of pulse signals of dripping solution are obtained, as a way to monitor the infusion rate. However, ultrasound monitoring device is hard to be implanted in small portable devices due to the obstacles in cost, size, power consumption and other aspects, but it usually be applied relatively large non-portable devices in some circumstances such as professional infusion pumps in hospital operation room, which are very expensive and requires high power consumption. These types of infusion pumps are not practical for the widely using in small family medical facility, military battlefield or refugee institution.

Device based on the optical perception technologies might involve placing optical transceivers at both sides of the dripping chamber. Taking advantage of the principle that droplets cause light attenuation and refraction during the dripping process, a group of pulse signals reflecting cycle of the dripping solution is obtained, as a way to monitor the infusion rate. However, the lightness perception devices have the following disadvantages: The optical transceivers might have to be protected from light and thus the dripping chamber where it transmit the light might need to be covered, and therefore it will hinder the visual operation and observation of the standard infusion through the dripping chamber, as well it cannot be effectively applied to the light-sensitive medical solution infusion. In additional, large amount of natural light, electric light and medical infrared light often interfere with the lightness perception monitoring process and it will reduce the accuracy of the monitoring infusion dripping rate; Plus, the need of continuous light emission requires high power consumption, which is not practical for certain infusion field condition. Some prior monitoring devices such as that described in U.S. Pat. No. 5,166,667 to Jen. This device uses control circuit for providing a light source for transmitting light through a wall of the drip chamber to each drop of fluid suspended from the end of the drip tube, and an optical system for receiving light transmitted through the drop and generating control signals to detect the flow rate of dripping in dripping chamber, which requires a light source to constantly illuminate the infusion solution during the infusion process.

Another example of the infusion fluid level sensing system is disclosed in U.S. Pat. No. 5,135,485 to Cohen et al. discloses an infusion fluid level sensing system by using a conductive plates attached the outside of the plastic infusion bag and connect to a circuit to detecting the change in the capacitance of the capacitor formed thereby due to the fluid level changes in the infusion bag during the infusion process. This device not only has the disadvantages inherent in a monitoring but also has several other problems in its implementation. The device has limited ability to accurately monitor the infusion flow rate by attaching the device to the infusion bag. It is well known that gravity infusion plastic bag size varies wildly and very deformable. In additional, it uses capacitance detector to detect the fluid level in the infusion bag and calculate the flow rate by monitoring the fluid level in the infusion bag, therefore the detected flow rate is very rough as well poor accuracy, and the infusion dripping rate is not capable to be detected and displayed in this device.

BRIEF SUMMARY

The present invention discloses an infusion-dripping rate monitoring technology, comprising a monitoring circuit device and monitoring method, which solves the technical problems as described above. This invention provide a new type of technology for monitoring the infusion dripping rate, which does not require covering the dripping chamber and thus does not interfere with the standard gravity infusion procedure. This invention device will be applicable to all types of the infusion (including light-sensitive medical solutions) and accurately display the infusion rate, so that medical stuffs may be able to set the more accurate infusion dripping rate than empirical visually estimation counted by eyes. The invention monitoring device has many advantage features such as high accuracy, compact and portable, low power consumption, and anti-interference etc. It overcome the shortcomings of existing technologies of the other infusion monitoring devices, such as interfering with the operation and observation of the infusion due to the light sensing infusion monitoring device covering the infusion dripping chamber, light interference significantly reducing the accuracy of the light sensing infusion monitoring device, limitation of the light sensing infusion monitoring device to monitor the light-sensitive medical solution, and large power consumption and so on.

The said monitoring circuit device includes a capacitor which are set as the two polar plates placed at the both side of the infusion tube above the dripping chamber, or alternatively the two metal plates might be set up as one metal plate placed around the infusion tube above the infusion dripping chamber and the other metal plate attached around the dripping chamber, a capacitance measurement unit electrically connected to the capacitor and is configured to measure the capacitance value of the capacitor; a micro control unit (MCU) electrically connected to the capacitance measurement unit; a LCD and a LED/buzzer electrically connected to the MCU. The described monitoring method is that we set the solution surface in the dripping chamber to a specific position so that the solution in the dripping chamber is conducted to the solution in the infusion tube above the dripping chamber at the last moment when the solution droplet is about to disconnect from the solution in the above tube, therefore, the capacitance values between the polar plates described above experience a pulse change in this process and the interval between the pulses corresponds to the infusion dripping rate. The monitoring circuit device will be able to continuous measure and analyze and display the calculated infusion dripping speed and send the alarm signal to the buzzer when the dripping speed is too fast, too slow or has been stopped.

Further, the described capacitor is a capacitor comprising a pair of metal plates, wherein the capacitor and the monitor device are clipped outside of the infusion tube above the dripping chamber as an integrated piece.

Further, the solution surface in the dripping chamber is adjusted to a specific height ranged from 6 mm to 9 mm to the dripping mouth above. Within such a range, every drop of solution droplets are able to be completely formed a shape with a standard volume (for example, the most common droplet shape of the gravity infusion is 0.05 ml/drops). At the last moment of the described solution droplet dripping from the infusion tube mouth to the infusion dripping chamber, every droplet will come into contact with the medical solution in the dripping chamber and the solution in infusion tube above at the same time in a very short period, and conduct the solution in these two part. Thus, the so described capacitance of the capacitor, the metal plates clipping on the infusion tube, will have a sudden pulse change of in value.

Further, the described capacitance measurement unit performs continuously measurement of the capacitance, and transmits a series of capacitance values with the pulse characteristics to the MCU for analysis, judgment and processing.

Further, when the MCU is analyzing and processing the series of capacitance values, in order to reduce noise interference and obtain accurate and reliable data, any discrete data with pulse period less than 300 ms and the data with adjacent pulses of mutual error greater than ±10% are discarded as invalid data (a 300 ms cycle corresponds to the infusion rate of 200 drops/minute, which is an infusion rate that is rarely reached during standard gravity infusion).

Further, the MCU calculates and extracts a pulse period based on a group of valid data with pulse characteristics, wherein this cycle is the actual cycle of solution dripping. The pulse frequency is then calculated as the reciprocal of the pulse period, which is multiplied by 60 to get the most common and important parameter in medical infusion, i.e., drops/min as the infusion rate.

Further, the MCU displays the infusion rate at real-time on the described LCD screen, for assisting the nurses to accurately set and adjust the initial infusion rate. At the same time, whenever the device detects dripping of the medical solution, the MCU controls the described LED to send a transient flash, to signal the caregiver of the normal infusion process.

Further, the system reserves a preset amount of time after the device turning on for the nurses to perform the initial adjustment. After this preset amount of time expires, the MCU will analysis and use a group of stable pulse data as the reference value to correspond of the infusion dripping rate. Then the MCU will continuously compare the real-time infusion dripping rate data with the reference value as described. Once an extreme change in the actual real-time infusion rate occurs compared to the baseline, or to a preset threshold (for example ±30% of the reference infusion rate), the MCU send the signal to the buzzer and the LED to light-sound alarms, to warning the caregivers for prompt actions.

Further, the system sets the average of a group of capacitance values after initial booting as the reference capacitance value, and compares the real-time capacitance values to this reference capacitance value intermittently during the subsequent monitoring process. When the real-time capacitance values loss the pulse feature but become consistently steady and is significantly lower than the reference capacitance value, it suggests that the medical solution in the infusion tube is empty. Thus, the system may use this method to determine whether the medical solution has been exhausted (when the infusion rate drops to 0), then the MCU send the signal to the buzzer and the LED to light-sound alarms, to warning the caregivers for prompt actions.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Hereinafter, the present invention will be described in detail with reference to the accompanying drawing regarding the area division principle, selection of measuring point, evaluation standard and construction of the system. It should be understood that drawing does not limit the scope of the present invention.

The present invention provides an infusion dripping rate monitoring technology, wherein the solution surface in the dripping chamber is set to a specific height, and a capacitor is made by two metal plates which are placed at both side of the infusion tube above the dripping chamber, or two metal plates are set as one plate placed around the infusion tube above the dripping chamber and another one placed around the infusion dripping chamber. At the very moment when a droplet of medical solution is about to drip down from the above infusion tube to the dripping chamber, it contacts and conducts the solution in the above infusion tube and the solution surface in the dripping chamber; hereby the so described capacitance values of the capacitor produce a sudden change with the pulse characteristics. Thus, measurement of the frequency of the pulse capacitance change signal will give the infusion dripping rate and a comprehensive live-time monitoring of the infusion dripping rate will be achieved. The present invention does not require covering the dripping chamber and interfering with the medical solution of the standard gravity infusion, and thus is applicable to all kinds of medical solution, various types of infusion methods and different types of infusion devices. Hereinafter, the present invention will be described in detail with reference to the accompanying drawing regarding the area division principle, selection of measuring point, evaluation standard and structure of the system. It should be understood that drawing does not limit the scope of the present invention.

Figure 1:
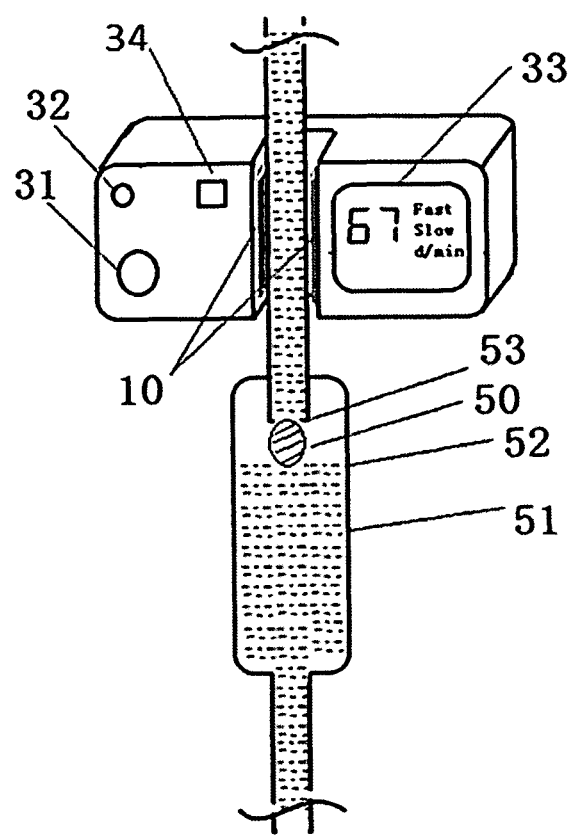
FIG. 1 is a schematic illustration of one embodiment of the described infusion dripping rate monitoring device.

FIG. 1 is a schematic illustration of one embodiment of the infusion rate monitoring device, comprising a metal polar plate capacitor 10 placed around the infusion tube above the dripping chamber 51, a buzzer of the monitoring device 31, a LED of the monitoring device 32, a LCD screen of the monitoring device 33. The monitoring device and the capacitor plates are clamped on the infusion tube as an integrated piece at the time of use, and the liquid surface level in the dripping chamber 52 is adjusted to a distance of 5mm to 9mm range to the dripping mouth 53.

Figure 2:
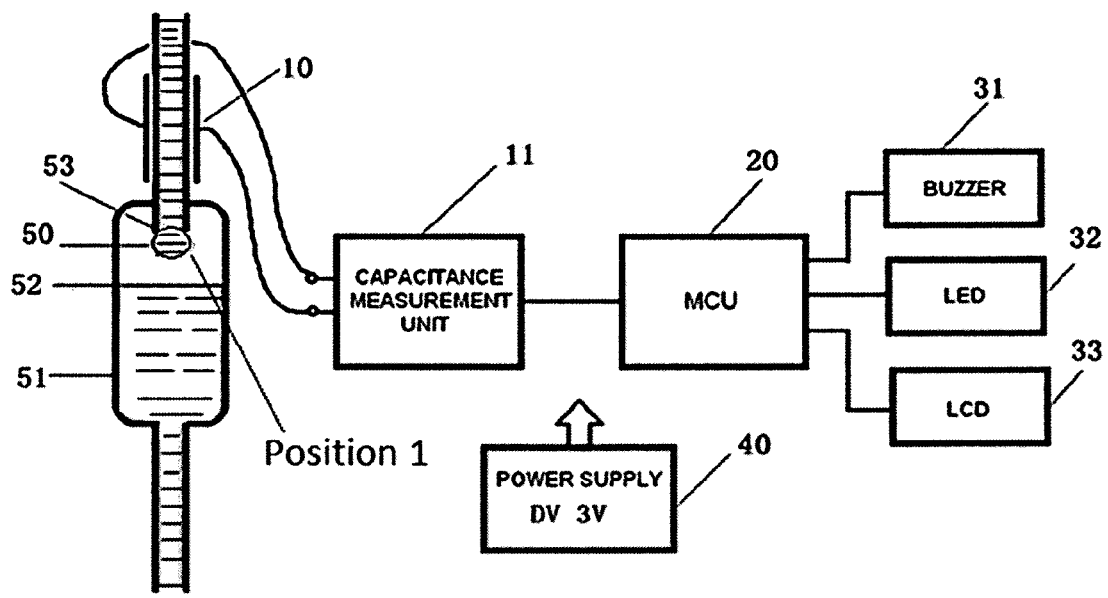
FIG. 2 is a schematic illustration of one embodiment of a circuit board with the solution droplet at Position 1 in dripping chamber as shown (when the droplet in the infusion tube has not dripped down from the above infusion tube to the dripping chamber yet).

FIG. 2 is a schematic illustration of one embodiment of a circuit board (when the droplet has not dripped down). Because of the liquid surface tension, the droplet 50 will not immediately drips down after pouring out of the dripping mouth 53, instead it continues to accumulate and bulge up around the dripping mouth. At this time, the liquid solution in the infusion tube above are not contacted nor conducted with the solution liquid in the dripping chamber 51, and the capacitance of the so described capacitor 10 is a relatively stable value.

Figure 3:
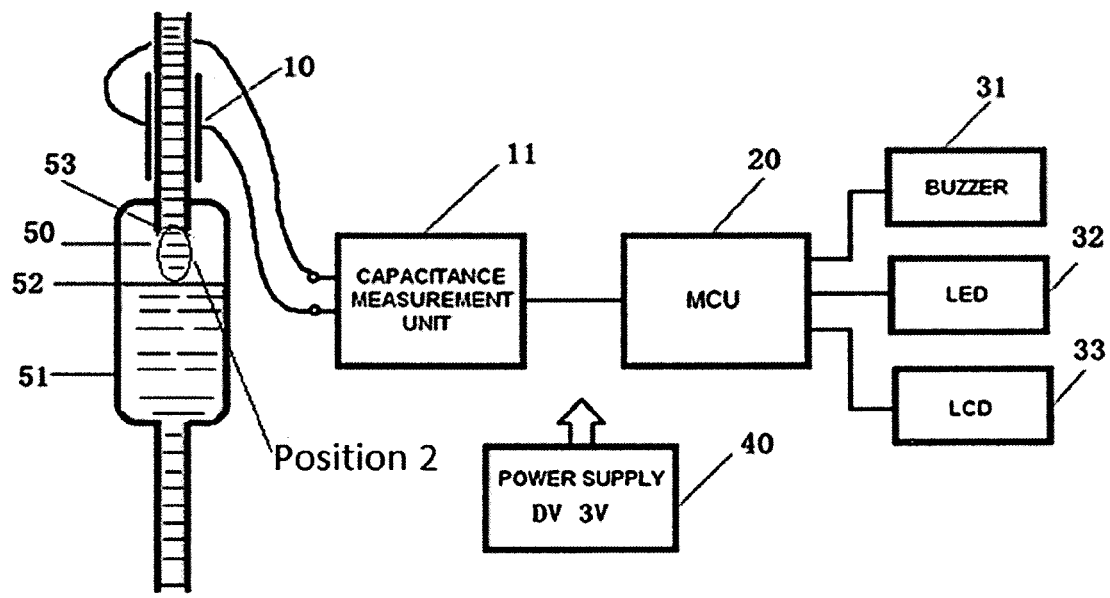
FIG. 3 is a schematic illustration of one embodiment of a circuit board with the solution droplet at Position 2 in dripping chamber as shown (at the moment when the droplet is dripping down from the above infusion tube to the infusion dripping chamber, and the droplet is temporarily conduct the two part of medical solution in the tube above and dripping chamber).

FIG. 3 is a schematic illustration of one embodiment of a circuit board (at the very moment when the droplet is almost dripping down). Because that ultimately the liquid surface tension of the liquid is unable to overcome gravity, the droplet 50 is going to drip down and detach from the dripping mouth 53. At this moment, the droplet 50 will temporarily contact the solution in the infusion tube above and the solution surface in the dripping chamber 51 and electrically conduct these two part of the liquid solution in a very short period. This conduction will change the composition and distribution of the dielectric between the metal polar plate capacitor 10, so the capacitance value of the capacitor 10 experiences a pulse sudden change periodically.

Figure 4:
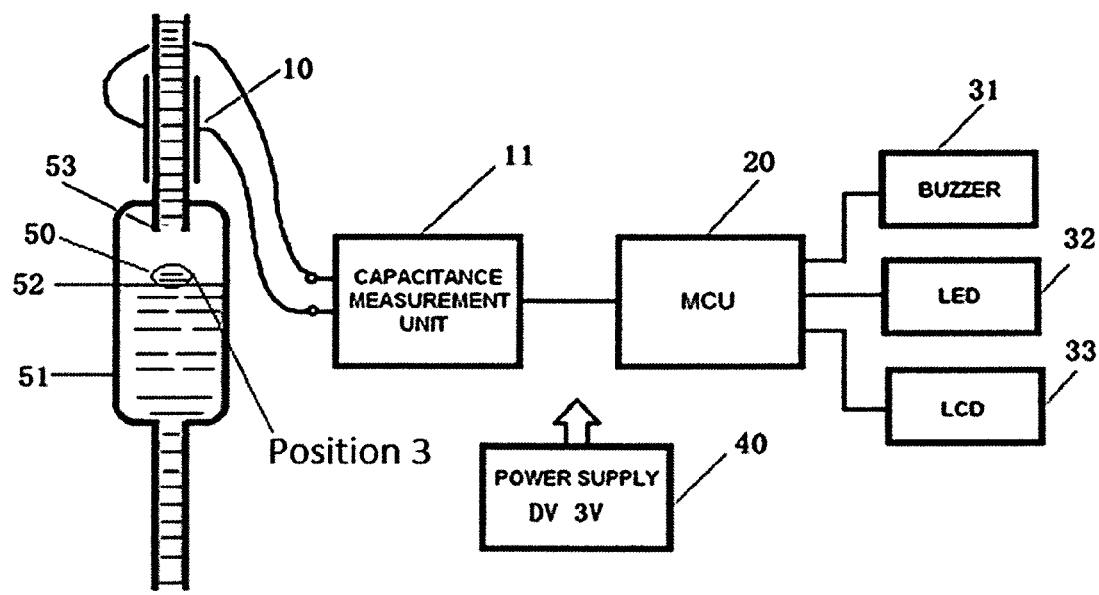
FIG. 4 is a schematic illustration of one embodiment of a circuit board with the solution droplet at Position 3 in dripping chamber as shown (after the droplet has been completely dripped down from the above infusion tube to the dripping chamber).

FIG. 4 is a schematic illustration of one embodiment of a circuit board (after the droplet has been completely dripped down from the above infusion tube). At this time the embodiment of a circuit board situation repeats similar to that in FIG. 2, i.e., the solution in the infusion tube above and the solution in the dripping chamber 51 is totally separated and not conducted, and the capacitance value of the capacitor 10 is returned to a relatively stable value same as that in FIG. 2.

Figure 5:
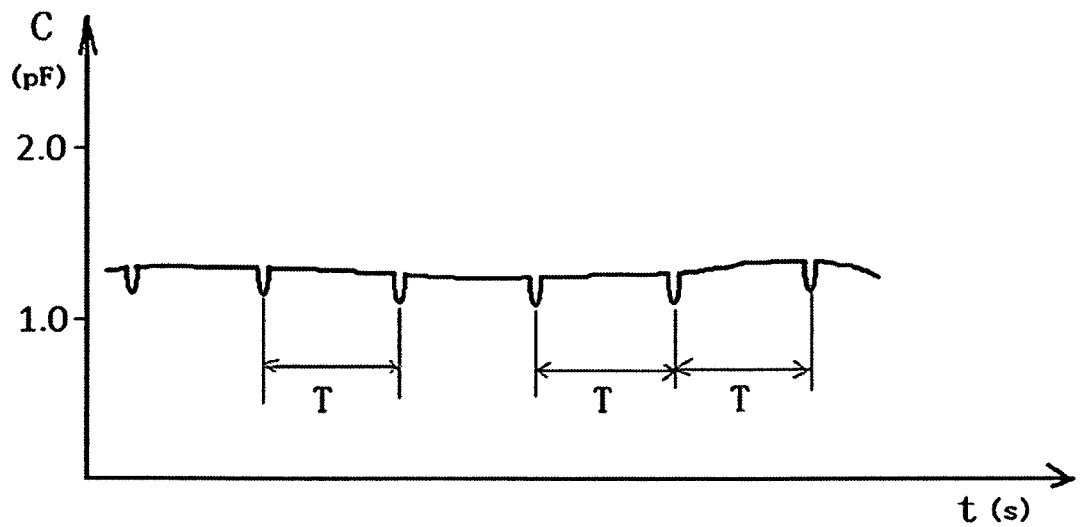
FIG. 5 is a schematic illustration of the capacitance values with pulse feature when the medical solution is periodically dripping.

Referring to FIG. 3 and FIG. 5, with the repeatedly dripping of the medical solution, the capacitance measurement unit 11 can measure and collect a series capacitance values plotted as shown in FIG. 5. Each pulse of the capacitance value in the plot chart corresponds to one droplet movement, and the interval T between each pulse is the period of the infusion dripping. MCU 20 continuously measures and analyzes these data and obtains and monitors the infusion dripping rate consequently.

Referring to FIG. 1, FIG. 2, FIG. 3, FIG. 4 and FIG. 5, MCU 20 continuously monitors and displays the infusion rate on the LCD 33; the MCU 20 is also programmed to set a stable infusion rate obtained within a certain period of time after booting as the baseline value, and continuously compares the real-time infusion dripping rate with this baseline value. When the change in real-time infusion rate exceeds the preset ratio threshold, it will send the signal to the buzzer 31 and the LED 32 to start audible and visual alarm.

Referring to FIG. 2, FIG. 3 and FIG. 4, since the entire system does not require emitting ultrasound or light, the power consumption is very low, so button batteries can be used as the power supply 40. Thus, the product is small and portable, favoring the use and generalization in the entire health care industry.

Figure 6:
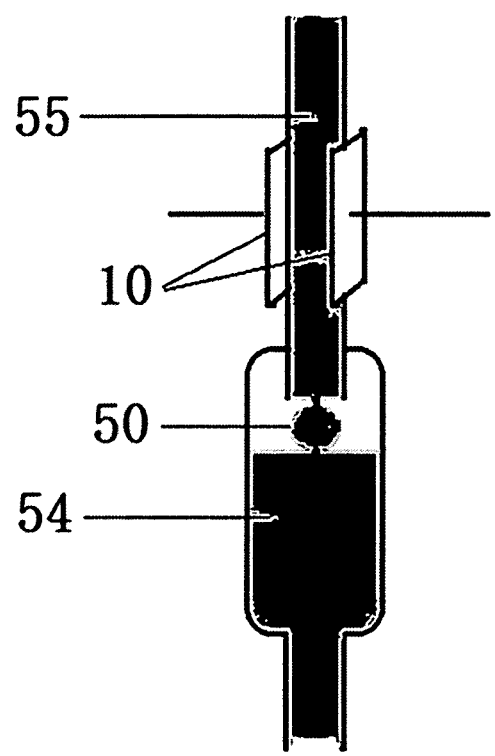
FIG. 6 is an analytic illustration of the described characteristics of the capacitance values.

FIG. 6 is analytic illustration of the described characteristics of the capacitance values between the designed capacitor. As shown in the Figure, capacitor 10 contains a pair of metal polar plates, and there are three dielectrics materials including the insulative plastic infusion tube, airs and the conductive liquid present in between. Based on common physical electronics knowledge we know that:

Assuming that the above-mentioned polar plates are symmetrical, parallel and vacuum is between the plates, then the capacitance value of the capacitor can be expressed as $C=\epsilon_0 *(S/d)$, with $\epsilon_0$ being the dielectric constant of vacuum, S being the plate area and d being the distance between the two plates.

Assuming that a single dielectric material is evenly filled between the two polar plates, the capacitance value of the capacitor can be expressed as $c=\epsilon*(S/d)$, with $\epsilon$ being the dielectric constant of the single dielectric material, S being the plate area and d being the distance between the two plates.

Assuming that a variety of dielectric materials are non-uniformly filled between the two polar metal plates as shown in FIG. 6 (including the edge extension), then the capacitance of the capacitor can be expressed as $C=\epsilon_e*(S/d)$, with $\epsilon_e$ being the equivalent dielectric constant of the multiple dielectric materials between the metal plates, the equivalent dielectric constant is determined by the variety of dielectrics and their specific distributions between the capacitor. S being the plate area and d being the distance between the two plates.

Referring to FIG. 6, apparently under the two stages when the droplet 50 conducts or does not conduct the solution in the infusion tube 55 and the solution in the dripping chamber 54, the composition and distribution of the two of three dielectric materials between the metal polar plates of the capacitor 10, which are the insulative plastic infusion tube and the airs between the capacitor 10, remains the staple condition, but the composition and distribution of the third dielectric material, the medical solution, is repeatedly change due to the droplet 50 periodically conducts the solution in the infusion tube 55 and the solution in the dripping chamber 54 as shown in FIG. 6. So the dielectric constant $\in_e$ under these two stages is not the same. Furthermore, based on the formula in [0039] $C=\in_e*(S/d)$, the area S of the capacitor 10 and the distance d between the capacitor 10 remains the same, so the capacitance value C in these two stages will be different due to the change of the dielectric constant $\in_e$. Therefore, at the moment when the droplet 50 is about to completely drip down and conduct the solution in the infusion tube 55 and the solution in the dripping chamber 54, the capacitance value of the capacitor 10 will have a pulse sudden change.

Referring to FIG. 6, similarly, when the medical solution 55 in the infusion tube is emptied and the infusion tube is filled with air, since the dielectric constant of air is much smaller than the liquid, the capacitance value of the described capacitor 10 will have a non-pulse steady, relatively large reduction of the capacitance between the capacitor 10. This relatively large change refers to the smaller pulse change described in [0040], and this relatively large decrease in the capacitance value can be designed for the monitoring device to determine that the medical solution has been finished.

The above description is one of the specific embodiments of the present invention. It should be pointed out that given the above disclosure, one skilled in the art could devise a number of improvements, variations and modifications that are within the scope and spirit of the invention disclosed herein. One example of such modification is that one of the metal polar plates can be placed tightly against the infusion tube above the dripping chamber while the other one can be placed outside of the lower part of the dripping chamber containing medical solution. By the same way as described above, each droplet will conduct the solution in the upper infusion tube and the solution in the dripping chamber at the last moment of droplet dripping down, and thus the described capacitance of the capacitor will also have a pulse change. This pulse change corresponds to the infusion dripping rate. Thus, these improvements, variations and modifications should also be included in the scope of the claims for the present invention.

What is claimed is:

1. A portable real time infusion monitoring device for detecting an infusion dripping flow rate in response to the movement of each infusion droplet dripping in an infusion dripping chamber and alarming when infusion dripping abnormalities occur during an intravenous therapy, the said monitoring device comprising:

a capacitor, made of two polar plates that are placed in communication with an infusion catheter above an infusion dripping chamber;

an capacitance measurement unit electrically connected to the said capacitor and configured to detect periodical capacitance value changes between the said capacitor during an intravenous therapy;

a micro control unit (MCU) electrically connected to the capacitance measurement unit that is configured to determine the infusion dripping flow rate by measuring the frequency of the capacitance change between the said capacitor during an intravenous therapy and compare the infusion dripping flow rate with a predetermined baseline values to determine infusion dripping rate abnormalities and generate an alarming signal when infusion abnormalities are detected;

a LCD displayer electrically connected to the said MCU, to display the infusion dripping flow rate during an intravenous therapy and generate a warning message when infusion dripping rate abnormalities are determined;

a LED light electrically connected to the said MCU that is designed to flash in response to each infusion droplet dripping in the infusion dripping chamber in order to facilitate monitoring the intravenous therapy in a dark environment and remains lit when infusion dripping flow rate stops or abnormalities are determined;

a buzzer electrically connected to the said MCU to instantly alarm when infusion dripping flow rate abnormalities are determined.

2. A method for monitoring infusion dripping flow rate and alarming for intravenous flow rate abnormalities, said method comprising the steps of:

i. providing a capacitance measurement device attached to an infusion catheter between an infusion solution bag and an infusion dripping chamber, adjusting the fluid level in the infusion dripping chamber to a specific height so that a formed infusion droplet is transiently connecting the liquid in the infusion catheter and the fluid in the infusion dripping chamber just prior to the infusion droplet dripping into the infusion dripping chamber, such that a transient change of the capacitance of the infusion catheter occurs due to the infusion droplet dripping into the infusion drop chamber;

ii. measuring the frequency of the infusion catheter's capacitance pulsatile change due to every infusion droplet repeatedly and transiently connect the liquid in the infusion catheter and the liquid in the infusion dripping chamber; and iii. calculating an infusion dripping flow rate based on time interval of the said pulsatile change of the capacitance values, and displaying real-time infusion dripping flow dripping rate on a LCD screen, and flashing a LED light in response to each infusion droplet dripping into the infusion dripping chamber; and iv. establishing an average dripping flow rate of the first few minutes as a baseline flow rate value, and comparing the actual dripping flow rate to the said baseline value, and generating an alarm signal when the said infusion dripping flow rate has been determined to be too fast, too slow or has been stopped or blocked.

3. The monitoring method described in claim 2, wherein the specific height is 6 mm to 9 mm from the bottom edge of infusion catheter to the liquid level in the infusion dripping chamber.

4. The monitoring method according to claim 2, wherein the system reserves a pre-set amount of time after device booting for healthcare worker to adjust the intravenous injection until a desired initial infusion dripping flow rate is confirmed.

5. The monitoring method according to claim 2, wherein the detecting step further comprises detecting the step of comparing real-time measured infusion dripping flow rate values with the said initial infusion rate confirmed by healthcare worker during an intravenous therapy, and determining an irregular infusion dripping flow rate when intravenous infiltration, intravenous embolism or too fast intravenous injection has been occurred, and generating an alarm signal when said irregular infusion dripping flow rate has been detected.

6. The monitoring method according to claim 2, wherein the detecting step further comprises detecting the zero infusion dripping flow rate in response to intravenous injection has been completed or stopped, and providing an alarm signal when a zero infusion dripping flow rate has been detected.

7. The monitoring method according to claim 2, wherein the detecting step further comprises providing an alarm signal when said capacitance value of the detected infusion catheter during an intravenous therapy loses the pulsatile change properties and become a steady value.

\* \* \* \* \*